United States Patent [19]

Westley

[11] 4,083,968
[45] Apr. 11, 1978

[54] THERAPEUTIC AGENT FOR IMPROVING CARDIOVASCULAR FUNCTION

[75] Inventor: John Westley, Mountain Lakes, N.J.

[73] Assignee: Hoffmann-La Roche, Nutley, N.J.

[21] Appl. No.: 647,849

[22] Filed: Jan. 9, 1976

Related U.S. Application Data

[63] Continuation of Ser. No. 489,978, Jul. 19, 1974, abandoned.

[51] Int. Cl.$^2$ .................... A61K 31/71; A61K 31/70; A61K 31/35
[52] U.S. Cl. ................................. 424/181; 424/180; 424/283
[58] Field of Search .................. 424/283, 180, 181

[56] References Cited

U.S. PATENT DOCUMENTS

| | | | |
|---|---|---|---|
| 3,715,372 | 2/1973 | Stempel et al. | 424/283 |
| 3,873,715 | 3/1975 | Pressman et al. | 424/283 |

*Primary Examiner*—Jerome D. Goldberg
*Attorney, Agent, or Firm*—Samuel L. Welt; Bernard S. Leon; William M. Farley

[57] ABSTRACT

Methods of and compositions for improving cardiovascular function utilizing as the active agent certain pharmaceutically acceptable salts, derivatives, isomers and homologs of lasalocid (formerly known as antibiotic X-537A) are disclosed.

2 Claims, No Drawings

THERAPEUTIC AGENT FOR IMPROVING CARDIOVASCULAR FUNCTION

This is a continuation of application Ser. No. 489,978 filed July 19, 1974, and now abandoned.

DESCRIPTION OF THE INVENTION

Certain salts, derivatives, isomers and homologs of lasalocid have been discovered to possess cardiovascular effecting properties in mammals. More particularly, we have discovered that these compounds cause a myocardial stimulation.

Lasalocid (formerly known as antibiotic X-537A) is a designation given to a crystalline antibiotic produced by a streptomyces organism isolated from a sample of soil collected at Hyde Park, Mass. Lyophilized tubes of the culture bearing the laboratory designation X-537 were deposited with the United States Department of Agriculture, Agriculture Research Service, Northern Utilization Research and Development Division, Peoria, Ill. The culture given identification number NRRL 3382 by the Agricultural Research Service, has been made available to the public through NRRL.

The antibiotic material, identified as lasalocid, upon laboratory analysis has been found to be 6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R), 5(S)-dimethyl-6-oxononyl}-2,3-cresotic acid, i.e., a compound represented by the formula

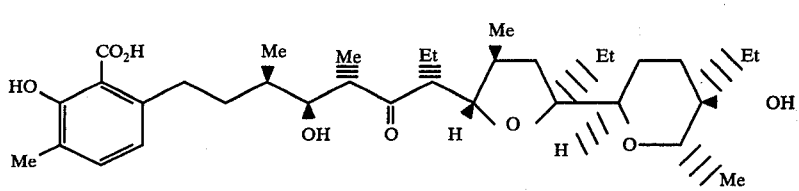

Lasalocid is prepared by growing the streptomyces organism in an aerated submerged culture, with the pH of the broth adjusted to about neutral, i.e., about 6.5 to 7.5. The medium utilized contains a nitrogen source such as yeast, a yeast derived product, corn meal, bean meal and the like, with soybean meal being the most preferred; and a carbohydrate source such as sugar, molasses, starch and the like with brown sugar being most preferred.

The fermentation is carried out at slightly elevated temperatures, i.e., between about 25° C. and 35° C., with the preferred incubation temperature being about 28° C. After an incubation of about 4 to 10 days, the fermentation broth is filtered and the antibiotic recovered by extraction. The preparation procedure for lasalocid and its derivaties is disclosed in U.S. Pat. No. 3,715,372, issued Feb. 6, 1973 and entitled "Derivatives of Antibiotic X-537A" by A. Stempel and J. Westley.

The active compounds of this invention which are all related to lasalocid, are represented by the formula

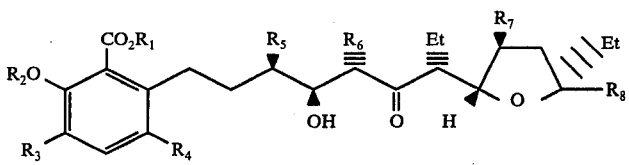

wherein $R_1$ is hydrogen, lithium, sodium, potassium, rubidium, cesium, barium, ammonium,

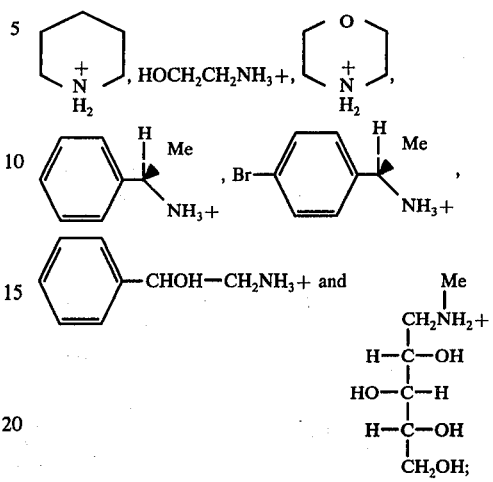

$R_2$ is hydrogen, acetyl, propionyl, butyryl, pentanoyl, hexanoyl, heptanoyl, octanoyl, decanoyl, benzoyl, benzoyl substituted by halogen, nitro or lower alkyl, or

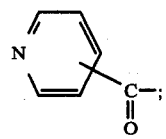

$R_3$, $R_5$, $R_6$, $R_7$ are methyl or ethyl with the proviso that when any one of $R_3$, $R_5$, $R_6$ or $R_7$ is ethyl, the other of $R_3$, $R_5$, $R_6$ and $R_7$ are methyl;
$R_4$ is hydrogen, halogen, phenylazo, diazo or phenylazo substituted by a member selected from the group consisting of halogen, nitro, lower alkyl and lower alkoxy; and
$R_8$ is a member selected from the group consisting of

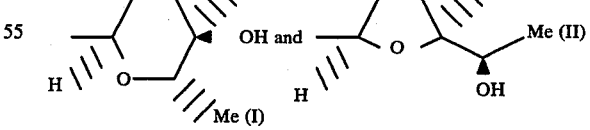

with the further provisos that:

1. when $R_1$ and $R_4$ are hydrogen; $R_3$, $R_5$, $R_6$, $R_7$, are all methyl and $R_8$ is (I), $R_2$ is neither hydrogen nor acetyl and 2. when $R_1$ and $R_2$ are hydrogen; $R_3$, $R_5$, $R_6$ and $R_7$ are all methyl and $R_8$ is (I), $R_4$ is neither bromine nor chlorine.

As used herein, the term "lower alkyl" denotes straight or branched chain hydrocarbon groups containing from 1 to 7 carbon atoms inclusive, such as methyl, ethyl, propyl, isopropyl, butyl, pentyl, hexyl and the like with groups containing from 1 to 4 carbon atoms being preferred. The term "lower alkanoyl" includes the acyl residue of lower alkanoic acids, preferably containing from 2 to 4 carbon atoms, such as acetyl, propionyl and the like. The term "halogen" includes fluorine, chlorine, bromine and iodine.

Representative of the active compounds are 3-methyl-2-nicotinoyloxy-6-[7(R)-[5(S)-ethyl-5-(5(R)-ethyltetrahydro-5-hydroxy-6-(S)-methyl-2H-pyran-2(R)-yl)tetrahydro-3(S)-methyl-2(S)-furyl]-4(S)-hydroxy-3(R),5(S)-dimethyl-6-oxononyl]-2,3-cresotic acid, ammonium salt.

5-Diazo-6-[7(R)-[5(S)-ethyl-5-(5(R)-ethyltetrahydro-5-hydroxy-6(S)-methyl-2H-pyran-2(R)-yl)-3(S)-methyl-2(S)-furyl]-4(S)-hydroxy-3(R),5(S)-dimethyl-6-oxononyl]-2,3-cresotic acid.

5-Phenylazo-6-[7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl]-2,3-cresotic acid.

2-(4-Bromobenzoyloxy)-3-methyl-6-[7(R)-ethyl-4(S)-hydroxy-3(R),5(S)-dimethyl-6-oxo-7-[5(S)-ethyl-3(S)-methyl-5-(5(R)-ethyl-5-hydroxy-6(S)-methyl-2(R)-tetrahydropyranyl)-2(S)-tetrahydrofuryl]heptyl]benzoic acid.

2-Benzoyloxy-3-methyl-6-{7(R)-ethyl-4(S)-hydroxy-

Preferred compounds are those represented by the formula

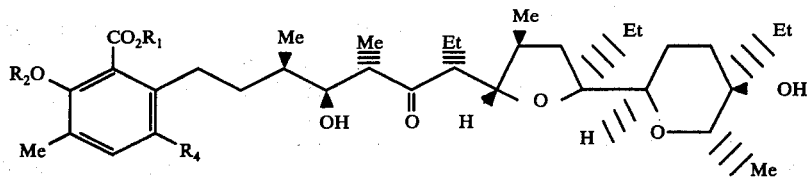

wherein $R_1$, $R_2$ and $R_4$ are as described above with the provisos that
a. when $R_1$ and $R_4$ are hydrogen, $R_2$ is neither hydrogen nor acetyl and
b. when $R_1$ and $R_2$ are hydrogen, $R_4$ is neither bromine nor chlorine.

Representative of these compounds are:

2-Hexanoyloxy-3-methyl-6-[7(R)-ethyl-4(S)-hydroxy-3(R),5(S)-dimethyl-6-oxo-7-[5(S)-ethyl-3(S)-methyl-5-(5(R)-ethyl-5-hydroxy-6(S)-methyl-2(R)-tetrahydropyranyl)-2(S)-tetrahydrofuryl]heptyl]-benzoic acid, sodium salt.

3-Methyl-2-propionyloxy-6-{7(R)-ethyl-4(S)-hydroxy-3(R),5(S)-dimethyl-6-oxo-7-[5(S)-ethyl-3(S)-methyl-5-(5(R)ethyl-5-hydroxy-6(S)-methyl-2(R)-tetrahydropyranyl)-2(S)-tetrahydrofuryl]-heptyl}benzoic acid, sodium salt.

2-Butyryloxy-3-methyl-6-{7(R)-ethyl-4(S)-hydroxy-3(R),5(S)-dimethyl-6-oxo-7-[5(S)-ethyl-3(S)-methyl-5-(5(R)-ethyl-5-hydroxy-6(S)-methyl-2(R)-tetrahydropyranyl)-2(S)-tetrahydrofuryl]heptyl}benzoic acid, sodium salt.

5-Iodo-6-[7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl]-2,3-cresotic acid, sodium salt.

2-Acetyloxy-5-bromo-3-methyl-6-[7(R)-ethyl-4(S)-hydroxy-3(R),5(S)-dimethyl-6-oxo-7-[5(S)-ethyl-3(S)-methyl-5-(5(R)-ethyl-5-hydroxy-6(S)-methyl-2(R)-tetrahydropranyl)-2(S)-tetrahydrofuryl]heptyl]-benzoic acid, sodium salt.

Other representative active compounds include:

Lasalocid B:

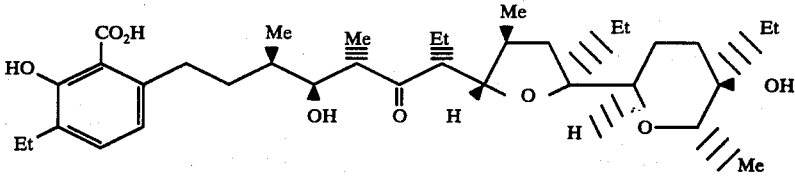

3(R),5(S)-dimethyl-6-oxo-7-[5(S)-ethyl-3(S)-methyl-5-(5(R)-ethyl-5-hydroxy-6(S)-methyl-2(R)-tetrahydropyranyl)-2(S)-tetrahydrofuryl]heptyl}benzoic acid.

6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furanyl]-4(S)-hydroxy-3(R),5(S)-dimethyl-6-oxononyl}2-hydroxy-3-ethylbenzoic acid.

Lasalocid C:

-continued

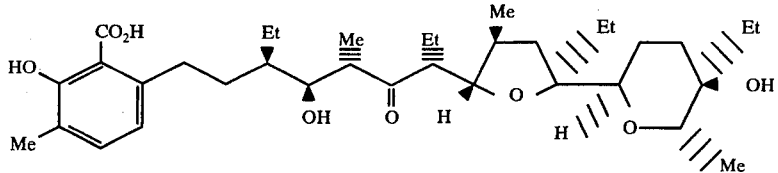

6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-3(R)-ethyl-4(S)-hydroxy-5(S)-methyl-6-oxononyl}-2,3-cresotic acid.

Lasalocid D:

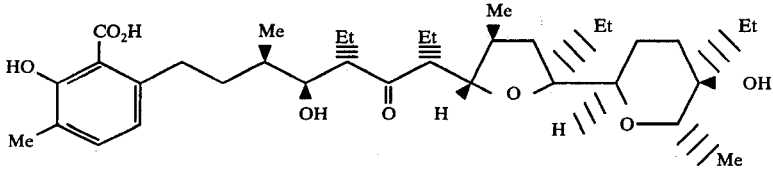

6-{7(R)-[5(S)-ethyl-5(5(R)-ethyltetrahydro-5-hydroxy-6(S)-methyl-2H-pyran-2(R)-yl)-tetrahydro-3(S)-methyl-2(S)-furyl]5(S)-ethyl-4(S)-hydroxy-3(R)-methyl-6-oxononyl}2,3-cresotic acid.

Lasalocid E:

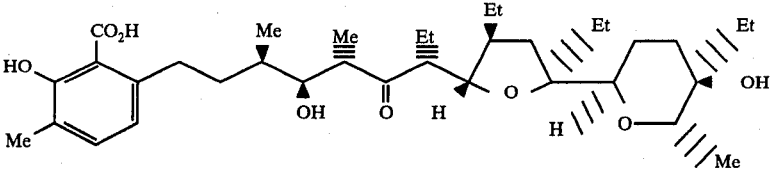

6-{7(R)-[5(S)-ethyl-5-(5(R)-ethyltetrahydro-5-hydroxy-6(S)-methyl-2H-pyran-2(R)-yl)tetrahydro-3(S)-ethyl-2(S)-furyl]-4(S)-hydroxy-3(R),5(S)-dimethyl-6-oxononyl}2,3-cresotic acid.

The invention also includes as an active compound, an isomer of lasalocid and derivatives thereof:

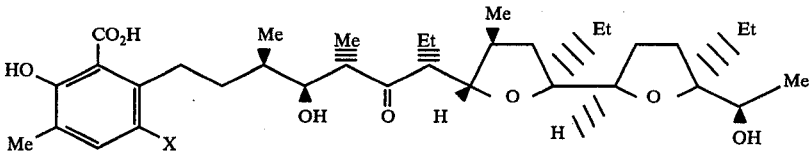

wherein X is hydrogen or halogen.

Representative of these active compounds are:

6-{7(R)-[5(S)-ethyl-5-(5(S)-ethyltetrahydro-5-(1(R)-hydroxyethyl)-furan-2(R)-yl)-tetrahydro-3(S)-methyl-2(S)-furyl]-4(S)-hydroxy-3(R),5(S)-dimethyl-6-oxononyl}-2,3-cresotic acid (iso-lasalocid A).

5-bromo-6-{7(R)-[5(S)-ethyl-5-(5(S)-ethyltetrahydro-5-(1(R)-hydroxyethyl)-furan-2(R)-yl)-tetrahydro-3(S)-methyl-2(S)-furyl]-4(S)-hydroxy-3(R),5(S)-dimethyl-6-oxononyl}-2,3-cresotic acid (bromo-iso-lasalocid A).

5-chloro-6-{7(R)-[5(S)-ethyl-5-(5(S)-ethyltetrahydro-5-(1(R)-hydroxyethyl)-furan-2(R)-yl-tetrahydro-3(S)-methyl-2(S)-furyl]-4(S)-hydroxy-3(R),5(S)-dimethyl- 6-oxononyl}-2,3-cresotic acid (chloro-iso-lasalocid A).

The active compounds useful in this invention form a variety of pharmaceutically acceptable salts. These salts are prepared from the free acid by methods well known in the art, for example, by reacting the free acid in solution with a suitable base or salt. Examples of pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonate and sulfates.

An amine suitable for forming an especially preferred group of salts is N-methylglucamine. Such salts are of special value because of their water-solubility which makes them amenable to parenteral use. The preparation of these salts and their water-solubility, included here for completeness although not part of this invention, is disclosed and claimed in U.S. patent application Ser. No. 489,976 filed on even date and entitled "Solubilization of Polyether Antibiotics, Their Derivatives, Isomers and Homologs in Aqueous Systems" by H. Newmark and J. Westley.

Representative of such salts are:

6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-2,3-cresotic acid, N-methylglucamine salt.

6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-2,3-cresotic acid, di(N-methylglucamine) salt.

5-bromo-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R)-,5(S)-dimethyl-6-oxononyl}-2,3-cresotic acid, N-methylglucamine salt.

5-bromo-6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-2,3-cresotic acid, di-(N-methylglucamine) salt.

5-chloro-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-2,3-cresotic acid, N-methylglucamine salt.

5-chloro-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-2,3-cresotic acid, di-(N-methylglucamine) salt.

2-acetyloxy-3-methyl-6-{7(R)-ethyl-4(S)-hydroxy-3(R),5(S)-dimethyl-6-oxo-7-[5(S)-ethyl-3(S)-methyl-5-(5(R)-ethyl-5-hydroxy-6(S)-methyl-2(R)-tetrahydropyranyl)-2(S)-tetrahydrofuryl]-heptyl}-benzoic acid, N-methylglucamine salt.

3-methyl-2-hexanoyloxy-6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-benzoic acid, N-methylglucamine salt.

2-(4-bromo-benzoyloxy)-3-methyl-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-benzoic acid, N-methylglucamine salt.

2-acetyloxy-5-bromo-3-methyl-6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-benzoic acid, N-methylglucamine salt.

3-methyl-2-pentanoyloxy-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-benzoic acid, N-methylglucamine salt.

2-heptanoyloxy-3-methyl-6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-benzoic acid, N-methylglucamine salt.

3-methyl-2-octanoyloxy-6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-benzoic acid, N-methylglucamine salt.

2-decanoyloxy-3-methyl-6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-benzoic acid, N-methylglucamine salt.

Active compounds for therapeutic treatment by improving cardiovascular function in which $R_3$, $R_5$, $R_6$ and $R_7$ are methyl; $R_2$ is hydrogen or acetyl and $R_4$ is hydrogen, bromine or chlorine and $R_8$ is

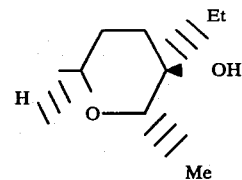

are covered in copending patent application Ser. No. 348,809, filed Apr. 6, 1973 and entitled "A Therapeutic Agent for Improving Cardiovascular Function" by B. Pressman and N. de Guzman.

Some of the specific compounds useful in this invention are known compounds and their preparation is disclosed in U.S. Pat. No. 3,715,372 entitled "Derivatives of Antibiotic X-537A" by A. Stempel and J. Westley.

Thus, compounds wherein $R_2$ is acetyl can be prepared from compounds wherein $R_2$ is hydrogen by using conventional acetylating agents such as acetic anhydride or acetyl chloride.

Compounds wherein $R_2$ is propionyl, butyryl or benzoyl can be prepared from compounds wherein $R_2$ is hydrogen by using propionic anhydride, butyric anhydride and benzoic anhydride, respectively.

Compounds wherein $R_4$ is chlorine, bromine or iodine can be prepared from compounds in which $R_4$ is hydrogen by any conveniently available halogenating technique, e.g., bromination with bromine, chlorination with chlorine or iodination with iodine monochloride.

Compounds wherein $R_4$ is nitro can be prepared from compounds wherein $R_4$ is hydrogen by treatment with nitric acid in the presence of glacial acetic acid.

Compounds wherein $R_4$ is phenylazo can be prepared from compounds wherein $R_4$ is hydrogen by treatment with a phenyldiazonium salt, previously prepared from sodium nitrite and aniline or a substituted aniline in dilute aqueous acid.

Other of these compounds are described in U.S. patent application Ser. Nos. 457,296, filed Apr. 2, 1973 and entitled "Homologs of Lasalocid A" by J. Westley, and 457,298, filed Apr. 2, 1974 and entitled "Iso-Lasalocid A" by J. Westley.

Compounds wherein $R_3$, $R_5$, $R_6$ and $R_7$ are methyl or ethyl (i.e., homologs of lasalocid A) can be prepared by fermentation of the streptomyces organism as described in the aforesaid U.S. patent application Ser. No. 457,296.

Iso-lasalocid A is prepared by the fermentation of the streptomyces organism as described in the aforesaid U.S. patent application Ser. No. 457,298.

The most significant desired criteria for chemical compounds used to treat chronic heart conditions, such as congestive heart failure, or emergency heart conditions, e.g., shock, heart failure, are that the compound should have a positive inotropic effect with little or no chronotropic effects and display minimal, if any, adrenergic action. Other desirable criteria are that the compounds have a rapid onset of action, require a small effective dose, are non-toxic at the effective doses, display a satisfactory duration of action, display a return to the original pre-drug values of cardiovascular activity, and continued identical response to subsequently repeated identical doses. It is also desirable that such compounds be amenable to oral or parenteral administration. The oral administration is particularly preferred for long term treatment of chronic diseases, e.g., congestive heart failure, while parenteral administration is the choice for emergency treatment, e.g., shock, acute heart failure.

The active compounds of this invention fulfill the desired criteria and are thus useful for stimulation of cardiovascular functions and treating such ailments as cardiogenic shock, septic shock and congestive heart failures.

For use as cardiovascular agents, the active agents are formulated, using conventional inert pharmaceutical adjuvant materials, into dosage forms which are suitable for oral or parenteral administration. Such dosage forms include tablets, suspensions, solutions, hard or soft capsules, dragees and the like. The identity of the inert adjuvant materials which are used in formulating the active compounds into oral and parenteral dosage forms will be immediately apparent to persons skilled in the art. These adjuvant materials, either inorganic or organic in nature, include, for example, water, dimethylsulfoxide, gelatin albumin, lactose, starch, magnesium stearate, preservatives, stabilizers, wetting agents, emulsifying agents, salts for altering osmotic pressure, buffers, etc. which can be incorporated, if desired, into such formulations.

The quantity of active agent which is present in any of the above described dosage forms generally varies from 5 to 100 mg. per unit dosage. The dosage administered to a particular patient is variable, depending upon the clinician's judgment using as the criteria the condition and size of the patient, the potency of the active agent and the patient's response thereto. An effective dosage amount of active agent can therefore only be determined by the clinician utilizing his best judgment on the patient's behalf.

Generally, parenteral doses should be from about 20 mg. to about 50 mg. for the average size man. Smaller persons or larger persons require adjustments due to size. Oral doses, usually capsules, but tablets can be used, generally are about twice the parenteral dose.

The frequency of the dose would depend upon the patient's condition. Chronically ill patients may require administration every 2 to 3 hours or once a day, depending on the severity of the disease and the patient's response.

Emergency patients frequently need only one dose of active compound, particularly those in shock.

The cardiovascular effects of the various derivatives of lasalocid are manifested by positive inotropic effects with minimal chronotropic effects. These effects are measured by the parameters of myocardial force of contraction, heart rate and arterial blood pressure. To obtain these measurements, dogs were anesthetized and catheters were introduced into the femoral artery and vein for recording femoral arterial blood pressure and for drug administration, respectively.

For example, Beagle hounds of either sex were anesthetized with intravenously administered thiopental sodium (15 mg./kg.) and barbital sodium (275 mg./kg.). Artificial respiration was maintained during surgical manipulation by using a Bird respirator (Mark 8). Myocardial force of contraction was measured by suturing a strain gauge arch to the surface of the right ventricle after opening the chest through the left 4th interspace. This procedure is described by Boniface et al., Resistance strain gauge arches for direct measurement of heart force in animals, Proc. Soc. Exp. Biol. Med., 84: 263–266 (1963). The chest was then closed by suturing. Pneumothorax was reduced and spontaneous breathing was permitted.

Electrocardiograms were recorded using lead 11. Heart rates were recorded on a Sanborn cardiotachometer by using the electrical signal of the "R" wave of lead 11. A Statham pressure transducer measured femoral artery blood pressure. These monitored parameters were recorded on an 8-channel Sanborn direct writing recorder.

The electrophysiological and hemodynamic responses of the dogs were measured at a time before, and at various time intervals after, intravenous injection of a drug. Solutions of the drugs were administered rapidly as a single injection by means of a polyethylene catheter placed in the femoral vein.

The following vehicle formulations were used to solubilize the drugs for intravenous injection.

| Formulation A | |
|---|---|
| Ingredient | per ml. |
| Propylene Glycol | 0.500 ml. |
| Alcohol, Anhydrous Ethyl | 0.100 ml. |
| Benzyl Alcohol | 0.015 ml. |
| Water | q.s. to 1 ml. |

| Formulation B | | |
|---|---|---|
| Ingredient | per ml. | per 2 liters |
| Carboxymethyl cellulose | 5 mg. | 10.0 gms. |
| Sodium Chloride | 9 mg. | 18.0 gms. |
| Tween ® 80 | 0.0039 mg. | 7.8 ml. |
| Benzyl Alcohol | 0.0086 mg. | 17.2 ml. |
| Water | q.s. to 1 ml. | q.s. to 2000 ml. |

Tween ®80 (Atlas Powder Co.), a non-ionic surface active agent, is a polyoxyalkylene derivative of sorbitan monooleate.

| Formulation C | |
|---|---|
| Ingredient | per ml. |
| Propylene glycol | 0.1 ml. |
| N-methylglucamine | 6.9 mg. |
| Benzyl Alcohol | 0.015 ml. |
| Water | q.s. to 1 ml. |

| Formulation D | |
|---|---|
| Ingredient | per ml. |
| Propylene glycol | 0.1 ml. |
| Benzyl Alcohol | 0.015 ml. |
| N-methylglucamine | 6.9 mg. |
| Glacial Acetic Acid | 0.005 ml. |
| Water | q.s. to 1 ml. |

Formulations C and D contain N-methylglucamine, an agent which solubilizes antibiotics of the polyether type. This use of such an agent, included here for completeness although not part of this invention, is disclosed and claimed in a co-pending U.S patent application Ser. No. 489,976 filed on even date herewith and discussed hereinabove.

Representative test compounds were evaluated for effects on heart rate, contractile force and mean arterial blood pressure. The results are set forth in the following Table.

TABLE I

| Compound | Vehicle Formulation | Dose (mg/kg) (i.v.) | Time Post-Drug (min.) | Inotropic Response (% Change/ Control) | Heart Rate (% Change/ Control) | Mean B.P. (% Change/ Control) |
|---|---|---|---|---|---|---|
| Iso-lasalocid A | D | 3.0 | 20 | 33 | −10 | 12 |
| | | 4.0 | 20 | 54 | +15 | 26 |
| Bromo-iso-lasalocid A, di-(N-methylglucamine) salt | water | 2.0 | 5 | −3 | −3 | −2 |
| | water | 4.0 | 5 | 14 | −4 | 0 |
| | water | 8.0 | 20 | 18 | 4 | 8 |
| Lasalocid, N-methylglucamine salt | D | 0.5 | 15 | 64 | 0 | 8 |
| | | 1.0 | 15 | 33 | 31 | 41 |
| Lasalocid, di-(N-methylglucamine) salt | water | 0.5 | 5 | 7 | 0 | 0 |
| | water | 1.0 | 15 | 7 | 7 | 15 |
| | water | 2.0 | 4 | 106 | 205 | 41 |
| Lasalocid hexanoate, di-(N-methylglucamine) salt | water | 0.5 | 5 | 0 | 0 | 0 |
| | water | 1.0 | 5 | 11 | 0 | 0 |
| | water | 2.0 (ml/kg) | 20 | 50 | 23 | 33 |
| Control | D | 0.05 (i.v.) | 5 | −18 | 0 | 0 |
| | | 0.10 (i.v.) | 5 | 0 | −4 | −3 |
| | | 0.20 (i.v.) | 15 | −13 | −4 | −2 |
| | | 0.30 (i.v.) | 5 | −11 | 0 | 3 |
| | | 0.40 (i.v.) | 5 | 25 | 4 | 9 |
| | | 0.80 (i.v.) | 15 | 25 | 0 | 6 |

The following Examples illustrate the invention.

EXAMPLE 1

Preparation of Lasalocid Homologs B, C, D, and E

The streptomyces organism was grown in aerated submerged culture in the shaken flasks. The pH of the broth was adjusted by the addition of KOH solution to 6.5–7.5, then the broth was sterilized. A tank fermentation was used wherein a 5–10% inoculum consisting of 3-day-old submerged growth from aerated bottles was used in the tank. The medium contained 2% soybean flour, 2% brown sugar, 0.1% $K_2HPO_4$ and 0.5% cornsteep liquor. The fermentation was carried out at 28° C. under positive air pressure, with air-flows of 5–10 cu. ft. of air per minute per 40- to 80-gallon liquid charge. The broth was harvested after 4 to 6 days fermentation, filtered, and the antibiotic was recovered by extraction. The extraction was carried out as follows:

204 Liters of broth were filtered and the wet filter cake was suspended in 100 liters of butyl acetate and the mixture was stirred overnight, at room temperature. The mixture was then filtered and the water layer was separated and discarded. The butyl acetate soolution, assaying 30 million Bacillus E units, was concentrated in vacuo to 3 liters, washed with 10% sodium carbonate solution, and dried with anhydrous sodium sulfate.

On further concentration to 300 ml. and dilution with 350 ml. of petroleum ether (B.P. 50°–60° C.), 41 g. of solid material, assaying 25 million Bacillus E. units separated. This solid material was then extracted in a Soxhlet apparatus with 4 liters petroleum ether (B.P. 50°–60° C.) for 40 hours. The extract was taken to dryness in vacuo, the crystalline residue suspended in petroleum ether and filtered. Repeated crystallization gave mother liquor enriched in homologs.

EXAMPLE 2

Isolation of Lasalocid Homologs B, C, D and E

A portion (equal to 22 g. solids) of the final mother liquors from the large scale preparation of Example 1 was chromatographed in a 200 tube (each 80 ml. capacity) counter current distribution apparatus. The sample was dissolved in 160 ml. of the mixed phases (heptane-ethyl acetate-methanol-water, 27:18:18:2) and the solution placed in the first two tubes. After 380 transfers, the following fractions were pooled and the solids recovered afte evaporation identified as:

A. Mixture of lasalocid homologs B, C, D and E
B. Lasalocid A
C. Isolasalocid A

Fraction A was dissolved in 20 ml. of the mixed phases of the solvent system heptane, ethyl acetate, ethanol, water and glacial acetic acid (10:5:9:3:1) and subjected to chromatography on a 500 tube counter current distribution apparatus. After 2800 transfers, approximately 200 mg. each of lasalocids B, C, D and E were separated and upon analysis had the following melting points:

Lasalocid B — Mp. 85°–87° C.
Lasalocid C — MP. 97°–100° C.
Lasalocid D — MP. 102°–104° C.
Lasalocid E — MP. 90° C.

EXAMPLE 3

Sodium Salt of Homolog Lasalocid E

Approximately 100 mg. of lasalocid E was dissolved in methylene chloride and treated with a saturated solution of aqueous sodium carbonate. The solvent layer was concentrated with hexane to give 104 mg. of the crystalline lasalocid E sodium salt (mp. 182°–182.5° C.).

EXAMPLE 4

Preparation of Iso-lasalocid A

The streptomyces organism was grown in aerated submerged culture in the shaken flasks. The pH of the broth was adjusted by the addition of KOH solution to 6.5–7.5, then the broth was sterilized. A tank fermentation was used herein, a 5–10% inoculum consisting of 3-day-old submerged growth from aerated bottles was used in the tank. The medium contained 2% yellow split peas, 1% cornstarch, 0.1% $K_2HPO_4$ and 2% lard oil. The fermentation was carried out at 28° C. under positive air pressure, with air-flows of 5–10 cu. ft. of air per minute per 40- to 80-gallon liquid charge. The broth was harvested after 6 days fermentation, filtered, and the antibiotic was recovered by extraction. The extraction was carried out as follows:

204 Liters of broth were filtered and the wet filter cake was suspended in 100 liters of ethyl acetate and the mixture was stirred overnight at room temperature. The mixture was then filtered and the water layer was separated and discarded. The ethyl acetate solution, assaying 30 million Bacillus E units, was concentrated in vacuo to 3 liters, washed with 10% sodium carbonate solution and dried with anhydrous sodium sulfate.

On further concentration to 300 ml. and dilution with 350 ml. of petroleum ether (B.P. 50°-60° C.), 41 g. of solid material, assaying 25 million Bacillus E units, separated. This solid material was then extracted in a Soxhlet apparatus with 4 liters petroleum ether (B.P. 50°-60° C.) for 40 hours. The extract was taken to dryness in vacuo, the crystalline residue suspended in petroleum ether and filtered. Iso-lasalocid A is found in the filtrate.

EXAMPLE 5

Isolation of Iso-lasalocid A

A portion of the concentrated filtrate from the large scale preparation of Example 1 was chromatographed on a 200 tube (each 80 ml. capacity) counter-current distribution apparatus. The sample was dissolved in 160 ml. of the mixed phases (heptane-ethyl acetate-methanol-water, 27:18:18:2) and the solution placed in the first two tubes. After 380 transfers, the following tubes were pooled and the solids recovered after the evaporation contained:
  A. Mixture of lasalocid homologs B, C, D and E
  B. Lasalocid A
  C. Crude Iso-lasalocid A Fraction C, which was in crude form and contained sodium and potassium as salts, was dissolved in methylene chloride and washed with 0.1 N HCl to convert it to the purified Iso-lasalocid A free acid.

The Iso-lasalocid A which was isolated had a melting point of 183°-185° C.

EXAMPLE 6

Preparation of the Sodium Salt of Iso-lasalocid A

Approximately 100 mg. of Iso-lasalocid A was dissolved in methylene chloride and treated with a saturated solution of sodium carbonate. The solvent layer was concentrated with hexane to give 104 mg. of the crystalline Iso-lasalocid sodium salt (m.p. 183°-183.5° C.).

EXAMPLE 7

Preparation of the Potassium Salt of Iso-lasalocid A

Approximately 387 mg. of Iso-lasalocid A was dissolved in 200 ml. of ethyl acetate and treated with 0.2 N KOH. The solvent layer was dried over $K_2CO_3$ and concentrated under vacuum to a colorless foam weighing approximately 369 mg.

EXAMPLE 8

Preparation of the Barium Salt of Iso-lasalocid A

Approximately 0.77 g. of Iso-lasalocid A was dissolved in methylene chloride and treated with a saturated solution of Ba $(OH)_2$. The solvent layer was separated and concentrated under vacuum to a foam weighing approximately 0.62 g.

EXAMPLE 9

Preparation of the Bromine Derivative of Iso-lasalocid A

To a solution of 3.672 g. of the sodium salt of Iso-lasalocid A in 500 ml. of methylene chloride at 3° C. was added slowly, over a period of 1 hour, 0.323 ml. of bromine in 50 ml. of methylene chloride. After 1 hour, the solution was allowed to slowly warm up to 15° C. and 1 liter of water was added. The solvent layer was removed, washed in turn with aqueous sodium bisulfite, aqueous sodium carbonate and water. The solution was dried over $Na_2SO_4$ and concentrated to an oil from which 2.1 g. of crystals were recovered after addition of acetone/hexane. The crystalline material was dissolved in methylene chloride and washed 1 N HCl. The solvent layer was concentrated to a small volume and after addition of acetone/hexane, the brominated Iso-lasalocid A was recrystallized from aqueous methanol. The brominated Iso-lasalocid A had a melting point of 185°-186° C.

The relative antibiotic activity of the bromo derivative in vitro testing against Bacillus TA was calculated by comparing a pure antibiotic lasalocid A and the bromo derivative of Iso-lasalocid A using the cup-plate agar diffusion technique. The bromo derivative had a percent relative in vitro activity of 75.

EXAMPLE 10

This example illustrates the preparation of a mono-(N-methylglucamine) salt, i.e., 6-{7(R)-[5(S)-ethyl-5-(5(R)-ethyltetrahydro-5-hydroxy-6(S)-methyl-2H-pyran-2(R)-yl)-tetrahydro-3(S)-methyl-2(S)-furyl]-4(S)-hydroxy-3(R),5(S)-dimethyl-6-oxononyl}-2,3-cresotic acid, N-methylglucamine salt.

Two g. of lasalocid (3.4 mmole) were dissolved in 50 ml. of ethylacetate and added to an equimolar amount of N-methylglucamine (0.66 g.) dissolved in 10 ml. of methanol:water (1:1). After the solution was stirred, the solvents were removed in vacuo to yield an oil. Crystallization of the oil from hexane yielded 2.4 grams of colorless powder.

Calc: $C_{41}H_{71}NO_{13}$(786.01): C, 62.56; H, 9.11; N, 1.78. Found: C, 62.99; H, 9.37; N, 1.52. $[\alpha]_D^{25}$ − 17.48° (C=1, $CH_3OH$)

EXAMPLE 11

This example illustrates the preparation of a di-(N-methylglucamine) salt, i.e., 6-{7(R)-[5(S)-ethyl-5-(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5(S)-dimethyl-6-oxononyl}-2,3-cresotic acid, di-(N-methylglucamine) salt.

To a solution containing 1.18 g. of lasalocid in methylene chloride was added 2 equivalents of N-methylglucamine (0.78 g.) in methanol. After the solution was stirred, the solvents were removed in vacuo to give an oil. Crystallization of the oil from acetone and hexane yielded 2.0 gms. of crystalline product.

M.P. 80°-105° C.:

Calc: $C_{48}H_{88}N_2O_{18}$(981.18): C, 58.75; H, 9.04; N, 2.85. Found: C, 58.64; H, 9.17; N, 2.87.$[\alpha]_D^{25}$ − 20° (C=1%, $CH_3OH$).

I claim:

1. A method for producing myocardial stimulation in a patient requiring such an effect which comprises parenterally administering to the patient an amount of the compound lasalocid, di-(N-methylglucamine) salt which is effective for producing myocardial stimulation.

2. A pharmaceutical parenteral composition for producing myocardial stimulation in patients requiring such effects comprising an inert non-toxic pharmaceutically acceptable carrier base and, as the active ingredient an amount which is effective in producing myocardial stimulation of lasalocid, di-(N-methylglucamine) salt.

* * * * *